(12) United States Patent
Kelley, II et al.

(10) Patent No.: US 10,195,206 B2
(45) Date of Patent: *Feb. 5, 2019

(54) TWO-COMPONENT PHARMACEUTICAL COMPOSITION FOR THE TREATMENT OF PAIN

(71) Applicant: BRIDGE THERAPEUTICS, INC., Pace, FL (US)

(72) Inventors: Alton Samuel Kelley, II, Mobile, AL (US); James Gregory Sullivan, Birmingham, AL (US)

(73) Assignee: BRIDGE THERAPEUTICS, LLC, Pace, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/855,592

(22) Filed: Apr. 2, 2013

(65) Prior Publication Data

US 2014/0080818 A1     Mar. 20, 2014

Related U.S. Application Data

(60) Division of application No. 12/571,990, filed on Oct. 1, 2009, now Pat. No. 8,410,092, which is a continuation of application No. 11/152,642, filed on Jun. 14, 2005, now abandoned.

(51) Int. Cl.
| | |
|---|---|
| *A61K 31/5415* | (2006.01) |
| *A61K 31/485* | (2006.01) |
| *A61K 31/192* | (2006.01) |
| *A61K 45/06* | (2006.01) |

(52) U.S. Cl.
CPC ........ *A61K 31/5415* (2013.01); *A61K 31/192* (2013.01); *A61K 31/485* (2013.01); *A61K 45/06* (2013.01)

(58) Field of Classification Search
CPC .......................... A61K 31/5415; A61K 31/192
See application file for complete search history.

(56) References Cited

U.S. PATENT DOCUMENTS

| | | | |
|---|---|---|---|
| 4,582,835 A | 4/1986 | Lewis et al. | |
| 4,636,498 A | 1/1987 | LaMattina | |
| 4,874,757 A | 10/1989 | Crawford et al. | |
| 4,906,625 A | 3/1990 | Sunshine et al. | |
| 5,272,149 A | 12/1993 | Stalling | |
| 5,474,783 A | 12/1995 | Miranda et al. | |
| 5,656,286 A | 8/1997 | Miranda et al. | |
| 5,914,129 A | 6/1999 | Mauskop | |
| 5,968,551 A | 10/1999 | Oshlack et al. | |
| 6,007,841 A | 12/1999 | Caruso | |
| 6,221,377 B1 | 4/2001 | Meyer et al. | |
| 6,231,886 B1 | 5/2001 | Reder et al. | |
| 6,294,195 B1 | 9/2001 | Oshlack et al. | |
| 6,375,957 B1 * | 4/2002 | Kaiko ............... | A61K 31/485 424/400 |
| 6,585,997 B2 | 7/2003 | Moro et al. | |
| 6,924,303 B2 | 8/2005 | Cooper | |
| 7,754,753 B2 | 7/2010 | Cooper | |
| 8,168,629 B2 | 5/2012 | Burch et al. | |
| 8,193,209 B2 | 6/2012 | Burch et al. | |
| 8,410,092 B2 * | 4/2013 | Kelley, II ............ | A61K 31/192 424/464 |
| 2002/0081333 A1 | 6/2002 | Oshlack et al. | |
| 2002/0098198 A1 | 7/2002 | Watts et al. | |
| 2003/0022876 A1 | 1/2003 | Ashton et al. | |
| 2003/0044446 A1 | 3/2003 | Moro et al. | |
| 2003/0096012 A1 | 5/2003 | Besse et al. | |
| 2003/0124191 A1 | 7/2003 | Besse et al. | |
| 2003/0138490 A1 | 7/2003 | Hu et al. | |
| 2003/0139698 A1 | 7/2003 | Hyson | |
| 2003/0180361 A1 | 9/2003 | Oshlack et al. | |
| 2003/0199439 A1 | 10/2003 | Simon | |
| 2004/0121001 A1 | 6/2004 | Oshlack et al. | |
| 2004/0121010 A1 | 6/2004 | Hirsh et al. | |
| 2004/0122104 A1 | 6/2004 | Hirsh et al. | |
| 2004/0132826 A1 | 6/2004 | Hirsh et al. | |
| 2004/0126416 A1 | 7/2004 | Reidenberg et al. | |
| 2004/0180036 A1 | 9/2004 | Ashton et al. | |
| 2004/0210280 A1 | 10/2004 | Liedtke | |
| 2006/0281775 A1 | 12/2006 | Kelley | |

OTHER PUBLICATIONS

Ashburn, Michael A. et al., "Management for Chronic Pain", Lancet 1999; 353: 1865-69.
Boeckstyns, Michael E.H. et al., "Piroxicam spares buprenorphine after total joint replacement", Acta Orthop Scan 1992; 63(6): 658-660.
Brookoff, Daniel, "Chronic Pain: 1. A New Disease?", Hospital Practice, Jul. 15, 2000, vol. 35, No. 7, pp. 45-52, 59.
International Search Report and Written Opinion issued in PCT/US2006/22643, dated Nov. 13, 2006 (9 pages).
Martell, Bridget A. et al., "Systematic Review: Opioid Treatment for Chronic Back Pain: Prevalence, Efficacy, and Association with Addiction", Annals of Internal Medicine, vol. 146, No. 2, Jan. 16, 2007, pp. 116-127, with Appendix pp. W-26-W-29.
Woolf, Clifford J. et al., "Neuropathic pain: aetiology, symptoms, mechanisms, and management", Lancet 1999: 353:1959-64.

* cited by examiner

*Primary Examiner* — Gina C Justice
(74) *Attorney, Agent, or Firm* — Faegre Baker Daniels LLP; Roberta Jean Hanson

(57) ABSTRACT

The present invention is directed to a pharmaceutical composition that includes a combination of about 2-5 milligrams of a non-steroidal anti-inflammatory drug and from about 2-30 milligrams of an opioid analgesic in a single pharmaceutical dosage unit that can provide effective chronic pain management with the added benefit of reduced side effects such as withdrawal and gastrointestinal disorders. The non-steroidal anti-inflammatory drug may be piroxicam and the opioid analgesic may be buprenorphine. The present invention also provides for a method of managing pain in a patient that includes administering the pharmaceutical composition previously described. The pharmaceutical composition previously described may be administered in a single or multiple dosage regimens.

28 Claims, No Drawings

TWO-COMPONENT PHARMACEUTICAL COMPOSITION FOR THE TREATMENT OF PAIN

CROSS REFERENCE TO RELATED APPLICATION

This application is a divisional of U.S. application Ser. No. 12/571,990, filed Oct. 1, 2009, now U.S. Pat. No. 8,410,092, which is a continuation of U.S. application Ser. No. 11/152,642, filed Jun. 14, 2005. These applications and patents are incorporated herein by reference in their entirety for all purposes.

The invention relates generally to a pharmaceutical dosage unit having a therapeutically effective amount of a non-steroidal anti-inflammatory drug in combination with a therapeutically effective amount of an opioid analgesic that can be used for the treatment of pain with reduced side effects such as opioid withdrawal and gastrointestinal irritation and damage. More particularly, the pharmaceutical dosage unit includes piroxicam in combination with buprenorphine for sublingual administration.

BACKGROUND OF THE INVENTION

Pain is prevalent. It is estimated that more than 50 million Americans live with chronic pain caused by various diseases or disorders, and each year nearly 25 million people suffer with acute pain as a result of injury or surgery. Furthermore, chronic pain has been said to be the most costly health problem in America. Estimated annual costs, including direct medical expenses, lost income, lost productivity, compensation payments, and legal charges are currently about $90 billion. And the numbers are rising. Estimates indicate that by 2030, 148 million people will have chronic conditions, and associated annual direct costs will rise to $798 billion. Thus, pain management has been identified as one of the most difficult challenges for the health care industry.

Non-steroidal anti-inflammatory drug NSAIDs (also referred to as non-narcotic analgesics) are administered for the treatment of mild to severe pain and in some instances are prescribed for continuous use in the treatment of acute or chronic inflammatory states such as rheumatoid arthritis and osteoarthritis. NSAIDs are well absorbed following oral administration but there is a high potential for adverse side-effects such as ulcerations, abdominal pain, cramping, nausea, gastritis, kidney disease, angiodema, pancreatitis, and even serious gastrointestinal bleeding and liver toxicity at the upper limits of their effective dose ranges. Thus, the ability to use higher dosages of NSAIDs is generally limited. Moreover, above each NSAIDs' upper limit or ceiling, administration of additional NSAID or use of combinations of NSAIDs does not usually increase the analgesic or anti-inflammatory effect.

Opioid analgesics (also referred to as narcotic analgesics) such as buprenorphine are often used when pain control with NSAIDs is ineffective. While narcotic analgesics vary considerably in their chemical structures and pharmacological properties, almost all suffer the disadvantages of tolerance and possible addiction with continued usage.

Narcotic analgesics are classified generally as narcotic agonists or narcotic antagonists. Drugs that activate receptors in the brain are termed agonists. Hence, a drug that activates an opioid receptor is termed an opioid agonist. The repeated administration of opioid agonists results in dose-dependent physical dependence and tolerance. Physical dependence manifests as a characteristic set of withdrawal signs and symptoms upon reduction, cessation, or loss of an active compound at an opioid receptor. These withdrawal signs and symptoms can include sweating, cramps, aches, lacrimation, diarrhea, rhinorrhea, piloerection, and pupillary dilation. A drug that binds to a receptor in the brain to block the receptor rather than activate it is termed an antagonist. Examples of opioid antagonists are naltrexone and naloxone. Partial agonists are drugs that activate receptors in the brain but not to the extent as full agonists. Buprenorphine is an example of a partial agonist (also referred to as a partial opioid agonist or opioid analgesic). It is the partial agonist properties of buprenorphine that contribute to its effectiveness in pain management and provide the added benefit of reduced dependence on and/or addiction to opioids. Consistent with its agonist action at opioid receptors, however, partial agonists such as buprenorphine are still abusable, particularly by individuals who are not already physically dependents on opioids.

Although NSAIDs and opioid analgesics are individually limited in their ability to effectively manage pain without inducing adverse side effects such as gastrointestinal disorders, dependence and/or addiction to, and withdrawal upon cessation or reduction, it has now been found that a pharmaceutical composition for sublingual administration having relatively low effective amounts of a NSAID such as piroxicam in combination with relatively high effective amounts of an opioid analgesic such as buprenorphine improves upon existing pain medications and provides the additional benefit of reduced side effects.

SUMMARY OF THE INVENTION

The present invention is directed to a pharmaceutical composition that includes a combination of a non-steroidal anti-inflammatory drug such as piroxicam and an opioid analgesic such as buprenorphine in a pharmaceutical dosage unit that provides safe and effective pain management with the added benefit that side effects such as gastrointestinal tract damage and withdrawal as a result of physical dependence and/or addiction are reduced. In one embodiment, the invention is a pharmaceutical combination of a low effective amount of piroxicam and a high effective amount of buprenorphine. In another embodiment, the pharmaceutical composition is a combination of about 2-5 milligrams of a non-steroidal anti-inflammatory drug such as piroxicam and about 2-30 milligrams of an opioid analgesic such as buprenorphine for sublingual administration.

The present invention also provides for a method of managing pain with reduced side effects in a patient that includes administering to the patient, in a single or multiple dosage regime, the pharmaceutical composition previously described.

DETAILED DESCRIPTION OF SPECIFIC EMBODIMENTS

The present invention is a pharmaceutical composition for managing pain that includes a combination of a non-steroidal anti-inflammatory drug ("NSAID") and an opioid analgesic in a single pharmaceutical dosage unit. As used herein, pain management includes the pain treatment and pain control. The present invention offers advantages over existing pain management compositions that include opioid analgesics and NSAIDs by providing safe and effective pain management with a reduction in side effects such as gastrointestinal tract damage and withdrawal as a result of physical dependence on and/or addiction to the opioid analgesic. In one embodiment of the present invention, the pharmaceutical composition is a combination of a NSAID such as piroxicam and an opioid analgesic such as buprenorphine in a single pharmaceutical dosage unit. In one embodiment, the pharmaceutical dosage unit may be administered sublingually.

NSAIDs vary widely in their chemical structure and in their biological profiles as analgesics, anti-inflammatory agents and anti-pyretic agents. Aspirin, acetaminophen and phenacetin have long been among the most commonly used NSAIDs. Other examples of NSAIDs for use in the present invention include ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid tolfenamic acid, diflunisal, flufenisal, piroxicam, meloxicam, sudoxicam or isoxicam, and mixtures thereof. Among the newer NSAID compounds are diflunisal (DOLOBID), ibuprofen (BRUFEN), naproxen (NAPROSYN), fenoprofen (FENOPRON), piroxicam (FELDENE), flurbiprofen, mefenamic acid (PONSTAN) and sulindac (CLINORIL). In one embodiment of the present invention, the NSAID is indomethacin, meloxican, ketoprofen, piroxicam, or combinations thereof. In a particular embodiment of the present invention the NSAID is piroxicam.

Piroxicam is 4-hydroxyl-2-methyl-N-2-pyridinal-2H-1,2-benzothiazine-3-carboximide 1,1-dioxide. Piroxicam occurs as a white crystalline solid that is soluble in alcohol and aqueous solutions and sparingly soluble in water, dilute acid and most organic solvents. Piroxicam exhibits a weakly acidic 4-hydroxy proton (pKa 5.1) and weakly basic pyridyl nitrogen (pKa 1.8). Piroxicam is available commercially as FELDENE in 10 mg and 20 mg capsules from Pfizer Inc., distributed by Pfizer Labs, New York, N.Y. Piroxicam has the molecular formula $C_{15}H_{13}N_3O_4S$ and the following structural formula:

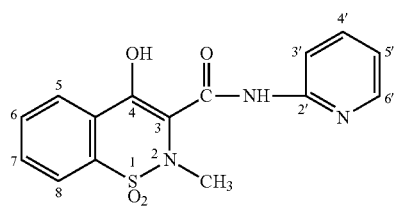

NSAIDs such as piroxicam generally possess anti-inflammatory, antipyretic and analgesic activities. The exact mechanism of action of NSAIDs and the relationship between chemical structure and analgesic, anti-inflammatory and anti-pyretic effect are not yet fully understood, but these properties may be mediated through the inhibition of prostaglandin synthesis. More specifically, NSAID compounds have been shown to be inhibitors of either or both of cyclooxygenase I (COX I) or cyclooxygenase II (COX II), which are involved in the synthesis of prostaglandins. Induction of the synthesis of COX II is associated with inflammatory processes and inhibition of COX II may result in the antipyretic and anti-inflammatory properties of NSAID compounds. Inhibition of constitutively-synthesized COX I may be associated with undesirable side effects such as gastric ulcers. Accordingly, selective inhibition of COX II rather than COX I may offer a therapeutic advantage.

While piroxicam is available for oral administration as FELDENE in 10 mg or 20 mg dosage units and is typically administered in amounts of 20 mg daily, the present invention is directed to relatively lower amounts (low effective amount) of NSAIDs such as piroxicam compared to the dosage amounts typically administered for pain management. Thus, as used herein, relatively low amount includes dosage amounts at about or below 5 mg. In one embodiment of the present invention, the NSAID is present in an amount of about 2-5 mg. In another embodiment, the NSAID is present in an amount of about 2-3 mg. In yet another embodiment of the present invention, the NSAID is present in an amount of about 2.5 mg. In still another embodiment, the NSAID is present in an amount of about 2 mg. Additionally, the NSAID of the present invention may be administered sublingually for absorption through mucous membranes in mouth. The low effective amount and sublingual administration of the NSAID may decrease the risk of side effects such as gastrointestinal disorders. In one embodiment, the side effects are gastrointestinal ulceration, abdominal pain, cramping, nausea, gastritis, kidney disease, angiodema, pancreatitis, gastrointestinal bleeding, liver toxicity, or combinations thereof.

Opioid analgesics also vary widely in their chemical structure and in their biological profiles. Presently known opioid analgesics include alfentanil, allylprodine, alphaprodine, anileridine, benzylmorphine, bezitramide, buprenorphine, butorphanol, clonitazene, codeine, cyclazocine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levallorphan, levorphanol, levophenacyl morphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papavereturn, pentazocine, phenadoxone, phenomorphan, phenazocine, phenoperidine, piminodine, piritramide, propheptazine, promedol, properidine, propiram, propoxyphene, sufentanil, tramadol, tilidine, salts thereof and mixtures thereof. In a particular embodiment of the present invention the opioid analgesic is buprenorphine.

Buprenorphine, a thebaine derivative that is legally classified as a narcotic, is 17-(cyclopropylmethyl)-α-(1,1-dimethylethyl)-4,5-epoxy-18,19-dihydro-3-hydroxy-6-methoxy-α-methyl-6,14-ethenomorphian-7-methanol.

Buprenorphine generally occurs as a white powder that is weakly acidic with limited solubility in water. Buprenorphine HCl has the molecular formula $C_{29}H_{41}NO_4HCl$ and the following structural formula:

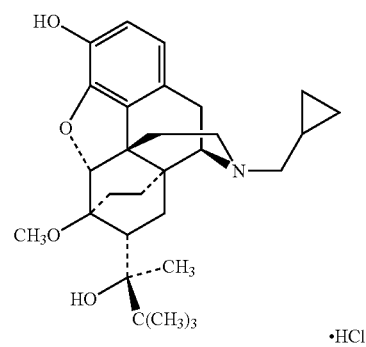

Buprenorphine is available commercially for parenteral administration under the name BUPRENEX (buprenorphine hydrochloride) from Reckitt Benckiser, Richmond, Va., and generically as buprenorphine from Abbott Laboratories. Buprenorphine is also available in sublingual tablets SUBUTEX (buprenorphine HCl) and SUBOXONE (buprenorphine HCl/naloxone HCl dihydrate) both available from Reckitt Benckiser.

Buprenorphine has poor oral and/or gastrointestinal bioavailability thus buprenorphine is usually given by injection, via a sublingual tablet, or as a transdermal patch. Abuse of buprenorphine has been reported to occur via the sublingual and intranasal routes but primarily via diversion of sublingual tablets to the injection route. Therefore, formulations of buprenorphine for opioid addiction and dependency treatment are generally in the form of sublingual tablets such as SUBUTEX and SUBOXONE.

The typical analgesic dose of buprenorphine is relatively low at amounts of 0.3-0.6 mg when injected (intramuscular or intravenous). Because the bioavailability of buprenorphine is less when administered orally or sublingually as compared to injections of buprenorphine, sublingual tablets are available in increased dosages of 2 mg or 8 mg. The present invention, however, may include a relatively high amount (high effective amount) of an opioid analgesic such as buprenorphine in a pharmaceutical dosage compared to dosages typically administered for pain management. In one embodiment, relatively high amount includes dosage amounts greater 0.6 mg of buprenorphine when injected or 8 mg of buprenorphine when administered as a sublingual tablet. Thus, in one embodiment of the present invention, an opioid analgesic such as buprenorphine is present in an amount of about 2-30 mg. In another embodiment, the opioid analgesic is present in an amount of about 10-30 mg. In still another embodiment, the opioid analgesic is present in an amount of about 10-15 mg.

Lower dosages of opioid analgesics such as buprenorphine are also effective in the present invention, however, particularly when administered in combination with a NSAID such as piroxicam. NSAIDs such as piroxicam have a prolonged half-life (approximately 50 hours), which results in the maintenance of relatively stable plasma concentrations throughout the day on once daily doses and to significant accumulation upon multiple dosing. Opioid analgesics such as buprenorphine also have an unusually long half-life (approximately 36 hours). As such, these NSAIDs and opioid analgesics may be combined in a single pharmaceutical dosage unit as a pharmaceutical combination dosage unit to provide safe and effective pain management with a reduction in side effects such as gastrointestinal tract damage and withdrawal as a result of physical dependence on and/or addiction to the opioid analgesic. This pharmaceutical combination dosage unit may include a low effective amount of a NSAID such as piroxicam and a high effective amount of an opioid analgesic such as buprenorphine where low effective amount of an NSAID is less than about 5 mg and high effective amount of an opioid analgesic is about 2-30 mg. Thus, in one embodiment, a NSAID such as piroxicam is present in an amount of about 2-5 mg and an opioid analgesic such as buprenorphine is present in an amount of about 2-30 mg. In another embodiment, the NSAID is present in an amount of about 2-3 mg and the opioid analgesic is present in an amount of about 2-15 mg. In still another embodiment, the pharmaceutical dosage combination includes about 2.5 mg of an NSAID and about 2 mg of an opioid analgesic.

The pharmaceutical dosage units of the present invention may be formulated for various forms of administration, including, for example, sublingual, mucosal, parenteral, intravenous, intramuscular, and/or transdermal administration and combinations thereof. Consistent with the various forms of administration, the pharmaceutical dosage unit can generally be formulated, for example, as a tablet, capsule, injection, and/or patch. In one embodiment of the present invention, the NSAID and opioid analgesic are combined in the same formulation of the pharmaceutical dosage unit. In another embodiment of the present invention, the NSAID and opioid analgesic are provided as individual formulations of the pharmaceutical dosage unit but administered such that the active ingredients are delivered to the patient simultaneously. In a particular embodiment of the present invention, the NSAID and opioid analgesic are combined in a sublingual tablet to be placed within the mouth and/or under the tongue.

Sublingual tablets are designed to dissolve very rapidly. Examples of such formulations include ergotamine tartrate, isosorbide dinitrate, isoproterenol HCl. The necessary ingredients for the pharmaceutical dosage unit may be processed in accordance with known methods, using or incorporating familiar coatings and additives as required. By way of example only, in addition to the pharmaceutically active components, a dosage unit may contain effective amounts of binders, fillers, disintegrants, sustained-release agents, diluents, anti-adherents, glidants, flow aids, plasticizers and lubricants, which are well known in the field of pharmaceutical processing. For instance, the formulation of these tablets may contain, in addition to the active agents, a limited number of soluble excipients, including a binder such as povidone or hydroxypropyl methylcellulose (HPMC), diluents such as lactose, mannitol, starch or cellulose, a disintegrant such as pregelatinized or modified starch, lubricants such as magnesium stearate, stearic acid or hydrogenated vegetable oil, a sweetener such as saccharin or sucrose and suitable flavoring and coloring agents. The process of making sublingual tablets generally involves moistening the blended powder components with an alcohol-water solvent system containing approximately 60% alcohol and 40% water and pressing this mixture into tablets.

A particular tablet-form formulation in accordance with the above-described embodiment of the present invention includes the following components:
Buprenorphine: 2 mg/tablet;
Piroxicam: 5 mg/tablet;
Sugar Base A: qs to desired tablet weight of approximately 215 mg; and
Coloring: 20 mg per 150 tablets,
where Sugar Base A includes the following components given by approximate wt.-% of Sugar Base A: DiPac (tableting sugar) 77 wt.-%, lactose 7 wt.-%, microcrystalline cellulose 5 wt.-%, flavoring 5 wt.-%, CrosPovidone 5 wt.-%, and magnesium stearate 1 wt.-%.

In an alternative tablet-form formulation, Naloxone is added to the formulation. Naloxone is an opioid antagonist that binds to a receptor in the brain to block the receptor rather than activate it. Thus, in some instances the inclusion of Naloxone may reduce opiate tolerance or even partially reverse tolerance if it occurs. Accordingly, Naloxone may be included to further reduce the abuse potential of the pharmaceutical dosage unit and withdrawal as a result of physical dependence and/or addiction. In this embodiment, the following components are included:
Buprenorphine: 2 mg/tablet;
Piroxicam: 5 mg/tablet;
Naloxone: 0.2 mg/tablet
Sugar Base A: qs to desired tablet weight of approximately 215 mg; and
Coloring: 20 mg per 150 tablets,
where Sugar Base A includes the following components given by approximate wt.-% of Sugar Base A: DiPac (tableting sugar) 77 wt.-%, lactose 7 wt.-%, microcrystalline cellulose 5 wt.-%, flavoring 5 wt.-%, CrosPovidone 5 wt.-%, and magnesium stearate 1 wt.-%.

The pharmaceutical dosage unit may be presented in a single dose or as divided doses administered at appropriate intervals, for example, as two, three, four or more sub-doses per day. In one embodiment, the pharmaceutical dosage unit may be formulated such that a single sublingual tablet is administered twice daily. In one embodiment, pharmaceutical dosage unit of the present invention once in the morning, such as at 8:00 am, and then again six hours later in the early afternoon or at approximately 2:00 pm.

Alternatively, the pharmaceutical dosage unit may formulated so that the active ingredients (i.e. the NSAID and the opioid analgesic) exhibit sustained-release characteristics upon administration to the patient. For example, the active ingredients may be delivered with an oral mucosal patch. Methods of making such patches are well known to one of skill in the art. In one embodiment the oral mucosal patch is prepared by homogeneously mixing buprenorphine and piroxicam with appropriate amounts of Carbopol 934, polyisobutylene, and polyisoprene using a two-roll mill and then compressing the mixture to the appropriate thickness. A membrane backing such as ethylcellulose is then applied to one side of the compressed material and circular disks, having an area of about 0.5 $cm^2$ and thickness of about 0.6 mm for example, may be punched from the material. The backing inhibits drug release from one side of the disk and reduces adhesion to opposing side tissues. The oral mucosal patches may be secured to mucosal buccal surfaces such as the gums, lips, and cheeks, and worn for extended periods. In one instance, the oral mucosal patches may be work for about 12 hours.

In another sustained release embodiment, the active ingredients may be delivered using a tablet-form dosage unit having a partially hydrophilic matrix which exhibits sustained release of at least one of the active components. In addition to the active ingredients, the tablet is comprised of, for example, ethylcellulose as a sustained-release agent and hydroxypropyl methylcellulose (HPMC) as a film former. Further, bulking agents such as microcrystalline cellulose and starch, a polyvinylpyrrolidone binder, silicon dioxide as an anti-adherent, dibutyl sebacate as a plasticizer, and magnesium stearate as a lubricant may be included. Using conventional processes, the listed ingredients, other than ethylcellulose, HPMC and dibutyl sebacate, are combined and pressed into a tablet. The tablet is then coated with the ethylcellulose, HPMC and dibutyl sebacate prior to administration of the tablet. When this tablet encounters an aqueous environment, such as the mucosal buccal surfaces, portions of the tablet coating dissolve, leaving a non-continuous film of water-insoluble ethylcellulose surrounding the remaining tablet core. The rate of diffusion of the active ingredients from the tablet core into the aqueous environment is determined by the concentration of ethylcellulose, HPMC and dibutyl sebacate in the coating.

As used in this specification and in the claims, the phrase "sustained release" indicates that an active component is released from the dosage unit over a period of time which is longer than its ordinary in vivo half-life, thus extending the presence of the component in a patient's system considerably beyond its ordinary half-life. Under such circumstances, the active component is said to "exhibit sustained-release characteristics." In contrast, the phrase "immediate release" indicates that an active component is released from the dosage unit within a short period of time (i.e., much shorter than its ordinary in vivo half-life); and decrease in concentration of the active component over time will be approximately described by its ordinary half-life. Under such circumstances, the active component is said to "exhibit immediate-release characteristics." In compositions of the present invention having more than one active component that is intended to exhibit sustained-release characteristics, an important consideration is that the release rate of each active component will need to be separately customized to produce the desired release profile, since the components will have different in vivo half-lives.

Another aspect of the present invention is a method of managing pain, the method including administering a pharmaceutical dosage unit having about 2-5 mg of a NSAID such as piroxicam in combination with about 2-30 mg of an opioid analgesic such as buprenorphine. The NSAID and opioid analgesic may be administered sublingually as a single pharmaceutical dosage unit or simultaneously in separate, sublingual pharmaceutical dosage units. In one embodiment, the pharmaceutical dosage unit is a sublingual tablet to be placed under the tongue.

The present invention also provides for a method of treating pain with reduced side effects, the method including administering a pharmaceutical dosage unit having about 2-5 mg of a NSAID such as piroxicam in combination with about 2-30 mg of an opioid analgesic such as buprenorphine. The NSAID and opioid analgesic may be administered sublingually as a single pharmaceutical dosage unit or simultaneously in separate, sublingual pharmaceutical dosage units. In one embodiment the side effects may include opioid withdrawal. Alternatively, the side effects may include, for example, ulcerations, abdominal pain, nausea, liver toxicity, gastrointestinal bleeding, kidney disease, or combinations thereof.

The present invention further provides a method of treating withdrawal, the method including administering a pharmaceutical dosage unit having about 2-5 mg of a NSAID such as piroxicam in combination with about 2-30 mg of an opioid analgesic such as buprenorphine. The NSAID and opioid analgesic may be administered sublingually as a single pharmaceutical dosage unit or simultaneously in separate, sublingual pharmaceutical dosage units. In one embodiment, the pharmaceutical dosage unit is a sublingual tablet to be placed under the tongue.

The appropriate dosages for administration to a patient for any of the compositions or methods of the present invention should be determined in accordance with accepted guidelines, such as those given by the Physician's Desk Reference. The patient's response to the pharmaceutical composition of the present invention may be monitored and the dosage adjusted as necessary.

The present invention is also directed to a method of treating pain in a human patient that includes administering to the human patient, in a single or multiple dosage regimen, a pharmaceutical dosage unit, where the dosage unit includes about 2-5 mg of a NSAID such as piroxicam in combination with about 2-30 milligrams of an opioid analgesic such as buprenorphine. The NSAID and opioid analgesic may be administered sublingually as a single pharmaceutical dosage unit or simultaneously in separate, sublingual pharmaceutical dosage units. In one embodiment, the pharmaceutical dosage unit is a sublingual tablet to be placed under the tongue. The method may additionally include monitoring the human patient to determine if the dosage regime is appropriate and either increasing or decreasing the dosage regimen as necessary.

The present invention offers significant advantages to patients already using high dosages of opioids, to patients seeking pain management methods to treat chronic pain without side effects or long term effects, and to patients seeking opioid addiction treatment. The present invention also provides physicians and patients an ability to switch from the present invention to a different pain management prescription without withdrawal issues.

Further objects and advantages of the invention will become apparent from a consideration of the examples and ensuing description which illustrate embodiments of the invention, it being understood that the foregoing statements of the objects of the invention are intended to generally explain the same without limiting it in any manner.

EXAMPLES

Example 1

Patients taking 15-80 mg/day of hydrocodone or 40-320 mg/day of oxycontin were switched to a pharmaceutical dosage unit including 2.5 mg piroxicam and 2 mg buprenorphine in a sublingual tablet. The sublingual tablets were administered to each patient twice daily. The patients perceived pain was measured using a visual analog scale (VAS).

Patients formerly taking 15-80 mg/day of hydrocodone experienced a 21% decrease in perceived pain scores after conversion. The perceived pain scores also remained stable when ½ dose reduction was attempted after a 22 day stabilization phase.

Patients that had been taking 40-320 mg/day of oxycontin experienced a 27% reduction in perceived pain 72 hours after conversion. No withdrawal or parasympathetic symptoms were noted in the oxycontin patients. The perceived pain scores remained stable when dose reduction was attempted after a 40-day stabilization phase.

The patients also generally reported feelings of being more in control of their lives, thinking clearer, sleeping better and being less lethargic than when they were taking hydrocodone or oxycontin.

Example 2

Patients taking 20-140 mg/day of methadone were also switched to a pharmaceutical dosage unit including 2.5 mg piroxicam and 2 mg buprenorphine in a sublingual tablet. These patients took an average of 6 days to convert before withdrawal was completely eliminated.

Patients taking 20-50 mg/day of methadone converted without ill effects, but did not take methadone the first day.

Patients taking 50-140 mg/day of methadone were first titrated down with Ultram (2-3 tablets every 4 hrs) for four days. Following this period, patients were given injections containing 0.03 mg buprenorphine and 60 mg torodol to see if further time was needed before the sublingual tablets containing buprenorphine and piroxicam could be started without risk of precipitating withdrawal. Significant withdrawal was observed in 18% of the patients on the first day the sublingual tablets were administered. Stomach tightness, nausea, and restless legs were the most common complaints from these patients. None of the patients experienced withdrawal on the second day the sublingual tablet was administered.

Pain scores using a VAS did not improve until week 2 with the methadone patients. By week 4, the methadone patients were willing to titrate down and by week 6 there was significant improvement in the VAS and no difference was noted with methadone and other opiate tolerant groups after the 6th week.

Example 3

Patients that had been taking piroxicam were also switched to a pharmaceutical dosage unit including 2.5 mg piroxicam and 2 mg buprenorphine in a sublingual tablet. The patients reported a 50% reduction in GI upset compared to when they were taking piroxicam orally.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A pharmaceutical formulation consisting essentially of piroxicam or meloxicam from 2 milligrams to 5 milligrams and buprenorphine from 2 milligrams to 15 milligrams, and a pharmaceutically acceptable excipient, for reduction of chronic pain in a subject.

2. The pharmaceutical formulation of claim 1, wherein the piroxicam or meloxicam concentration is 3.75 milligrams.

3. The pharmaceutical formulation of claim 1, wherein the formulation contains piroxicam.

4. The pharmaceutical formulation of claim 1, wherein the buprenorphine concentration is 2.5 milligrams.

5. The pharmaceutical formulation of claim 1, wherein the buprenorphine concentration is 5.0 milligrams.

6. The pharmaceutical formulation of claim 1, wherein the pharmaceutical formulation is delivered to the subject by sublingual, mucosal, parenteral, intravenous, intramuscular, transdermal administration and combinations thereof.

7. The pharmaceutical formulation of claim 1, wherein the formulation manages chronic pain with reduced side effects in the subject.

8. The pharmaceutical formulation of claim 7, wherein the side effect that is reduced is gastrointestinal ulceration, abdominal pain, cramping, nausea, gastritis, kidney disease, angiodema, pancreatitis, gastrointestinal bleeding, liver toxicity, or combinations thereof.

9. The pharmaceutical formulation of claim 7, wherein the side effect that is reduced is opioid withdrawal.

10. The pharmaceutical formulation of claim 1, further comprising naloxone.

11. A method for reducing chronic pain in a subject comprising, administering a pharmaceutical composition consisting essentially of piroxicam or meloxicam from 2 milligrams to 5 milligram and buprenorphine from 2 milligrams to 15 milligrams, and a pharmaceutically acceptable excipient to the subject for reduction of chronic pain in the subject.

12. The method of claim 11, wherein the subject has opioid tolerance.

13. The method of claim 11, wherein the pharmaceutical composition is administered to the subject sublingually.

14. The method of claim 11, wherein the pharmaceutical formulation is administered to the subject one or more times per day.

15. The method of claim 11, wherein the pharmaceutical formulation is administered twice daily to the subject.

16. The pharmaceutical formulation of claim 1, wherein the buprenorphine concentration is 7.5 milligrams.

17. The pharmaceutical formulation of claim 1, wherein the buprenorphine concentration is 10.0 milligrams.

18. The pharmaceutical formulation of claim 1, wherein the formulation contains meloxicam.

19. The pharmaceutical formulation of claim 1, wherein the formulation contains meloxicam at a concentration of 3.75 milligrams and buprenorphine at a concentration from 2.5 milligrams to 10 milligrams.

20. The pharmaceutical formulation of claim 1, wherein the formulation contains meloxicam at a concentration of 3.75 milligrams and buprenorphine at a concentration of 2.5 milligrams.

21. The pharmaceutical formulation of claim 1, wherein the formulation contains meloxicam at a concentration of 3.75 milligrams and buprenorphine at a concentration of 5.0 milligrams.

22. The pharmaceutical formulation of claim 1, wherein the formulation contains meloxicam at a concentration of 3.75 milligrams and buprenorphine at a concentration of 7.5 milligrams.

23. The pharmaceutical formulation of claim 1, wherein the formulation contains meloxicam at a concentration of 3.75 milligrams and buprenorphine at a concentration of 10.0 milligrams.

24. A pharmaceutical composition of buccally-deliverable formulation consisting essentially of meloxicam at a concentration of 3.75 milligrams and buprenorphine at a concentration from 2 milligrams to 15 milligrams, and a pharmaceutically acceptable excipient.

25. The pharmaceutical formulation of claim 24, wherein the buprenorphine concentration is 2.5 milligrams.

26. The pharmaceutical formulation of claim 24, wherein the buprenorphine concentration is 5.0 milligrams.

27. The pharmaceutical formulation of claim 24, wherein the buprenorphine concentration is 7.5 milligrams.

28. The pharmaceutical formulation of claim 24, wherein the buprenorphine concentration is 10.0 milligrams.

* * * * *